United States Patent [19]
Asrican

[11] 4,192,293
[45] Mar. 11, 1980

[54] CARDIAC ASSIST DEVICE

[76] Inventor: Manfred Asrican, Baldwin Farms South, Greenwich, Conn. 06830

[21] Appl. No.: 939,343

[22] Filed: Sep. 5, 1978

[51] Int. Cl.² ............................................. A61H 29/00
[52] U.S. Cl. ..................................... 128/1 D; 128/64
[58] Field of Search ............... 128/1 D, DIG. 3, 24.2, 128/24.5, 64; 3/1.7

[56] References Cited
U.S. PATENT DOCUMENTS

| | | | |
|---|---|---|---|
| 3,455,298 | 7/1969 | Anstadt | 128/64 |
| 3,587,567 | 6/1971 | Schiff | 128/64 |
| 3,590,815 | 7/1971 | Schiff | 128/64 |
| 3,613,672 | 10/1971 | Schiff | 128/64 |

*Primary Examiner*—Willis Little
*Attorney, Agent, or Firm*—Charles E. Temko

[57] ABSTRACT

A cardiac assist device which operates by cyclically exerting pressure through an implanted inflatable sheath, which surrounds the myocardium. The sheath is rigid and encloses a bladder or plurality of bladders into which a fluid, either in the form of an inert gas or a liquid is pulsed, with a time displacement curve similar or identical to the contraction-distension characteristics exhibited normally by the myocardium during a cardiac cycle. Pulsing is triggered by the EKG R-spike of the patient which operates a valve. In order to provide adequate fluid volume for the required pressure through the valve, an elastic fluid reservoir is provided.

6 Claims, 5 Drawing Figures

CARDIAC ASSIST DEVICE

BACKGROUND OF THE INVENTION

This invention relates generally to the field of surgical devices, and more particularly to an improved permanently implanted cardiac assist device for mechanically supporting the left ventricular pumping function of a failing human heart.

Various previous attempts to compensate for the loss of the natural pumping capacity of the heart by external assist devices are known in the art. It is also known to provide a total heart replacement by organic transplant or by substitution of a mechanical device. The problems arising from organic transplant are well-known and require little discussion. There have been two principal problems involved with mechanical devices, which are not readily overcome.

One problem is the occurrence of hemolysis caused by the continuous contact of the blood of the patient with intrinsically foreign materials. The second is a mechanical one, namely the difficulty of providing adequate power sources for the mechanical device in a practical and convenient fashion.

Some progress has been made over the last decade. In the Patent to Russo, U.S. Pat. No. 3,518,702, granted July 7, 1970, there is disclosed an implantable body-actuated artifical heart system which is powered and regulated by the chest and breathing muscles. The patent to Thoma, U.S. Pat. No. 4,034,742 granted July 12, 1977, shows a device, the operation of which is keyed to the electrocardiogram of the patient. The Cieszynski U.S. Pat. No. 4,078,267 granted Mar. 14, 1978, discloses a pump with a capacity four times that of the heart which operates at ¼ the normal heart frequency.

Reference is made to my confidential disclosure document filed in the U.S. Patent and Trademark Office on May 18, 1978, under No. 071297.

SUMMARY OF THE INVENTION

Briefly stated, the invention contemplates the provision of an improved cardiac device of the class described in which the function of the heart is assisted rather than replaced. The device includes an implanted rigid sheath which surrounds the myocardium, the inner surface of which supports a distensible bladder or series of bladders. A reciprocating pump is positioned externally and is continuously driven by respiration movement of the diaphragm of the patient. The pump feeds an elastic reservoir through a one-way valve. A second valve controlled electronically by the EKG of the patient is in series with conduit means interconnecting the reservoir and the bladder. Upon signal, a quantity of fluid under pressure is pulsed to the sheath to inflate the bladder which in turn compresses the myocardium. Fluid returns through a second one-way valve to the pump for recirculation. A safety by-pass is provided between the input and return conduits in order to safeguard against unappropriately high pressures and volumes of fluid being forced into the sheath.

The electronically controlled second valve may be powered by small batteries, but since the amperage and voltage requirement for satisfactory operation are very small, it is also possible to use diaphragm movement to power a small generator comprising merely a coil of wire and a permanent magnet periodically moved in either direction through the coil. The output of the coil, after rectification, is used to charge a small capacitor which is periodically discharged to provide current.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENT

Figure 1:
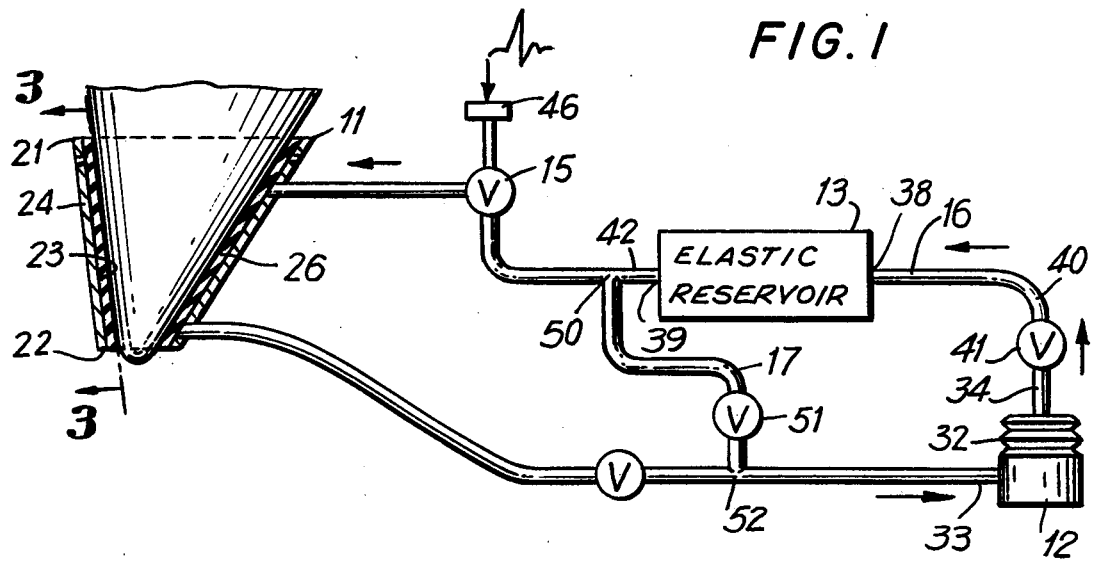
FIG. 1 is a schematic view of an embodiment of the invention.

In accordance with the invention, the device, generally indicated by reference character 10, comprises broadly: an inflatable sheath element 11, a reciprocating pump element 12, an elastic reservoir element 13, a heartbeat controlled valve element 15, conduit means 16 and pressure relief means 17.

The sheath element 11 is preferably formed of stainless steel or body-compatible synthetic resinous materials. It is generally of hollow frust-conical configuration, and is bounded by an upper continuous edge 21, a lower continuous edge 22 and inner and outer surfaces 23 and 24, respectively. A plurality of attachment holes 25 are provided to permit suturing in position using surgical techniques well known in the art.

Disposed on the inner surface 23 is an annular bladder 26, the outer surface 27 of which is adapted to directly contact the surface of the myocardium, and the inner surface 28 of which contains a pressurized fluid.

The reciprocating pump element 12 may be of any suitable type adapted to be driven by the breathing movement of the wearer. It includes a bellows 32 having an inlet 33 and an outlet 34, and is suitably mounted, such as e.g. by fixation within the thoracic cavity of the chest of the patient.

The reservoir element 13 is also surgically secured within the thoracic or abdominal space, and has a capacity equal to or less than that of the left ventricle. It is of relatively thick elastomeric material, so as to be capable of maintaining substantial pressure built up by repeated cycles of the pump element 12. It includes an inlet connection 38 and an outlet connection 39. An inlet conduit 40 is provided with a one-way valve 41, while an outlet conduit 42 communicates with the valve 15.

The valve 15 may be operated from a fluidic valve, or may be electrically operated using a battery-powered solenoid (not shown). An electrocardiogram pickup 46 controls the solenoid using solid state switches, again of known type.

In order to control excessive pressures within the reservoir, and maintain a substantially constant pressure in the bladder during cyclic operation, a T connection 50 is provided, which leads to a safety valve 51 and a second T connection 52, thereby permitting a direct return of excess pressure to the pump. Since the amount of fluid present in the system is fixed, this bleeding will normally be sufficient to maintain the pressure within prescribed limits.

Figure 2:
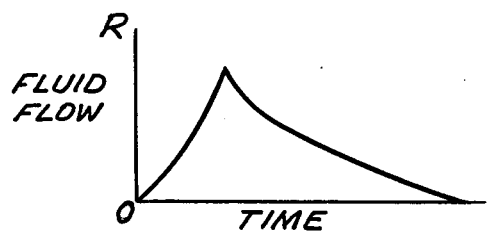
FIG. 2 is a flow diagram showing the pulsatile flow of fluid within the device.
Figure 3:
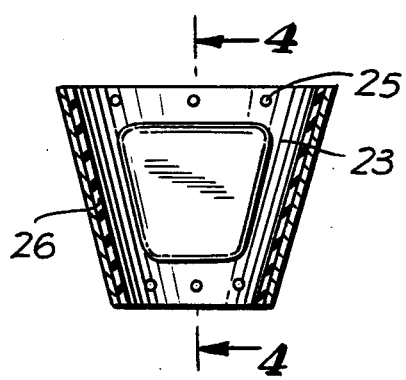
FIG. 3 is a sectional view as seen from the plane 3—3 in FIG. 1.
Figure 4:
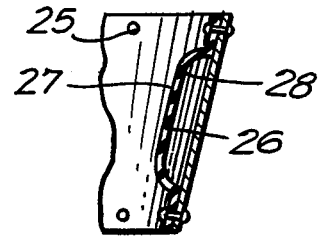
FIG. 4 is a fragmentary sectional view as seen from the plane 4—4 in FIG. 3.

During operation, the reservoir will remain in substantially inflated condition, and contracts to a relatively limited degree upon the occurrence of each pulse. The amount of fluid flow required for such pulse is relatively small, and the valve element 15 opens extremely quickly, and closes almost as quickly, in a manner illustrated in the graph in FIG. 2. The fluid pressure is not responsible for total contraction of the myocardium, but rather the expansion of the bladder 26 assists the natural action of the heart.

Where the degree of assistance is relatively small, it is possible to regulate the valve such that it operates not in synchronism with each heartbeat, but in synchronism with every second, third or fourth heartbeat, and, where necessary, means (not shown) may be included to limit the excursion of the pump to provide only that degree of pumping action consistent with such operation.

It may thus be seen that I have invented a novel and highly useful improvement in the cardiac assist art, in which in less than severe cases, the necessity for organic transplant is avoided. Although the device is preferably totally implanted, all of the elements are of relatively simple, trouble-free construction, and may be suitably covered with non-irritating materials. Surgical implantation is a relatively simple procedure, since no part of the circulatory system need be disturbed.

Figure 5:
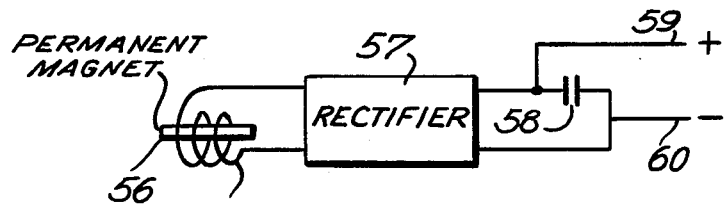
FIG. 5 is a schematic view showing circuitry for a diaphragm operated electrical generating means.

Referring to FIG. 5 in the drawing, there is schematically illustrated a small electrical generating means which may be formed as a part of the pump element 12. As has been mentioned, the power requirements for both the valve 15 and pickup 46 are very small, and can be fully accommodated by providing a small wire coil 55 and permanent magnet 56 which are mounted on relatively moving parts of the pump element. The output is fed to a small rectifier 57 which in turn charges a capacitor 58 periodically tapped through leads 59 and 60. As the diaphragm is continuously moving, and the pump is continuously in operation, the storage capacity of the capacitor may be relatively small. By full wave rectification, the inflow of current to the capacitor is substantially continuous.

I wish it to be understood tht I do not consider the invention limited to the precise details of structure shown and set forth in this specification, for obvious modifications will occur to those skilled in the art to which the invention pertains.

I claim:

1. An improved cardiac assist device comprising: a hollow rigid sheath of generally frusto-conical configuration adapted to be surgically implanted to surround the myocardium of a patient; an inflatable bladder mounted upon the inner surface of said sheath, and having means for input and return flow of a pressurized fluid from an external source; a reciprocating pump adapted to be worn by said patient, and driven by respitation movement of the diaphragm of said patient; an elastic reservoir connected in series with said pump, a valve in series with said reservoir and communicating with said bladder; means sensing the heartbeat of said patient and providing a signal controlling said valve in synchronism therewith; and conduit means for returning fluid from said bladder to said pump.

2. A device as set forth in claim 1, further comprising safety valve means for relieving excess fluid pressures in said reservoir to said pump.

3. A device as set forth in claim 1, further characterized in said pump having electrical generating means associated therewith for powering a pacemaker.

4. A device as set forth in claim 1, further characterized in said pump having means generating electromotive power connected thereto.

5. A device as set forth in claim 4, further characterized in said last mentioned means including a permanent magnet core and a coil surrounding said core; movement of said pump varying the relative position of said core and coil.

6. Improved means for generating electromotive power for use on the body of a wearer comprising: a reciprocating means adapted to be worn by a patient, and driven by respitation movement of the diaphragm of said patient, said reciprocating means including a permanent magnet core and a coil surrounding said core, movement of said reciprocating means serving to vary the relative position of said core and coil, to generate an electromotive force in said coil.

* * * * *